United States Patent
Koehler et al.

(10) Patent No.: US 9,466,135 B2
(45) Date of Patent: Oct. 11, 2016

(54) RECONSTRUCTION OF A REGION-OF-INTEREST IMAGE

(75) Inventors: Thomas Koehler, Norderstedt (DE); Claas Bontus, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 981 days.

(21) Appl. No.: 13/388,068

(22) PCT Filed: Jul. 9, 2010

(86) PCT No.: PCT/IB2010/053155
§ 371 (c)(1),
(2), (4) Date: Jan. 31, 2012

(87) PCT Pub. No.: WO2011/021116
PCT Pub. Date: Feb. 24, 2011

(65) Prior Publication Data
US 2012/0141006 A1     Jun. 7, 2012

Related U.S. Application Data
(60) Provisional application No. 61/235,373, filed on Aug. 20, 2009.

(51) Int. Cl.
G06K 9/00 (2006.01)
G06T 11/00 (2006.01)
A61B 6/00 (2006.01)

(52) U.S. Cl.
CPC ............ *G06T 11/006* (2013.01); *A61B 6/5258* (2013.01); *G06T 2211/424* (2013.01); *G06T 2211/432* (2013.01)

(58) Field of Classification Search
CPC .................. G06T 7/0012; G06T 2207/10081
USPC ................. 250/363.04, 363.05, 363.07, 393; 378/4, 7, 8, 14, 15, 16, 19, 20; 382/128, 131
See application file for complete search history.

(56) References Cited

U.S. PATENT DOCUMENTS

| | | | |
|---|---|---|---|
| 4,550,371 A * | 10/1985 | Glover et al. | 378/4 |
| 5,565,684 A * | 10/1996 | Gullberg et al. | 250/363.04 |
| 6,339,223 B1 * | 1/2002 | Motomura et al. | 250/363.07 |
| 6,426,989 B2 * | 7/2002 | Grass et al. | 378/4 |
| 6,850,587 B1 | 2/2005 | Karimi et al. | |

(Continued)

FOREIGN PATENT DOCUMENTS

| JP | 58206726 A | 12/1983 |
| WO | 2006064404 A2 | 6/2006 |
| WO | 2008152562 A1 | 12/2008 |

OTHER PUBLICATIONS

Hsieh, J., et al., "A novel reconstruction algorithm to extend the CT scan field-of-view," Med. Phys., 31 (9): pp. 2385-2391, Sep. 2004.*

(Continued)

*Primary Examiner* — Vu Le
*Assistant Examiner* — Xuemei Chen

(57) ABSTRACT

A method and system to perform region-of-interest (ROI) reconstruction is provided, even if the original projection data are truncated. The reconstruction is performed on a superset of the ROI, including the ROI as well as other areas which are outside the scan field-of-view of the imaging system but still within the imaging bore.

19 Claims, 7 Drawing Sheets

(56) References Cited

U.S. PATENT DOCUMENTS

| | | | |
|---|---|---|---|
| 7,358,727 B1* | 4/2008 | Angelos | 324/307 |
| 7,465,930 B2* | 12/2008 | Joung | 250/363.05 |
| 7,507,968 B2* | 3/2009 | Wollenweber et al. | 250/363.07 |
| 7,515,676 B2* | 4/2009 | Zamyatin | 378/4 |
| 7,526,060 B2 | 4/2009 | Ziegler | |
| 7,653,171 B2 | 1/2010 | Kunze et al. | |
| 7,672,424 B2* | 3/2010 | Ziegler et al. | 378/19 |
| 7,675,038 B2* | 3/2010 | Ray et al. | 250/363.04 |
| 7,683,341 B2* | 3/2010 | Bai et al. | 250/393 |
| 7,711,083 B2* | 5/2010 | Heigl et al. | 378/20 |
| 7,737,406 B2* | 6/2010 | Vija et al. | 250/363.04 |
| 7,782,997 B2* | 8/2010 | Koehler et al. | 378/4 |
| 7,929,742 B2* | 4/2011 | Maltz | 382/128 |
| 8,013,307 B2* | 9/2011 | Ye et al. | 250/363.04 |
| 8,121,245 B2* | 2/2012 | Pan | A61B 6/032 378/2 |
| 8,155,415 B2* | 4/2012 | Faul | A61B 6/032 382/128 |
| 8,218,715 B2* | 7/2012 | Sauer et al. | 378/4 |
| 8,385,621 B2* | 2/2013 | Koehler et al. | 382/131 |
| 8,396,274 B2* | 3/2013 | Bontus et al. | 382/131 |
| 8,406,373 B2* | 3/2013 | Graham et al. | 378/16 |
| 8,433,119 B2* | 4/2013 | Deykoon | 382/131 |
| 8,582,855 B2 | 11/2013 | Koehler | |
| 8,600,139 B2* | 12/2013 | Zhang et al. | 382/131 |
| 2008/0019473 A1 | 1/2008 | Koehler | |
| 2008/0219534 A1 | 9/2008 | Faul et al. | |
| 2009/0060121 A1* | 3/2009 | Ziegler et al. | 378/8 |
| 2009/0122954 A1* | 5/2009 | Bruder | 378/14 |
| 2009/0274265 A1* | 11/2009 | Koehler et al. | 378/15 |
| 2010/0208964 A1* | 8/2010 | Wiegert et al. | 382/131 |
| 2013/0294572 A1* | 11/2013 | Jaffray et al. | 378/7 |

OTHER PUBLICATIONS

Zamyatin, A., et al., "Extension of the reconstruction field of view and truncation correction using sinogram decomposition," Med. Phys., 34(5): pp. 1593-1604, May 2007.*

Bruder, H., et al., "Efficient extended field of view (eFOV) reconstruction techniques for multi-slice helical CT," SPIE Proceedings vol. 6913, 69132E, Mar. 2008.*

LaRiviere, P. J.; Monotonic iterative reconstruction algorithms for targeted reconstruction in emission and transmission computed tomography; 2006; IEEE Nuclear Science Symposium Record; M12-8; 2924-2928.

Ziegler, A., et al.; Iterative reconstruction of a region of interest for transmission tomography; 2008; Med. Phys.; 35 (4)1317-1327.

* cited by examiner

RECONSTRUCTION OF A REGION-OF-INTEREST IMAGE

CROSS REFERENCE TO RELATED APPLICATIONS

This application claims the benefit of U.S. provisional application Ser. No. 61/235,373 filed Aug. 20, 2009, which is incorporated herein by reference.

The present application relates generally to the imaging arts, and in particular a method and system to perform maximum likelihood region-of-interest (ROI) reconstruction even if the original projection data are truncated. In contrast to previously known maximum likelihood or other more general iterative ROI reconstructions, this reconstruction is performed on a superset of the ROI. The superset of the ROI or the region-to-iterate contains areas outside the scan field-of-view but still within the imaging bore of the imaging system, where objects have been found by means of an extended field-of-view reconstruction. The novel method described here has application in many different kinds of imaging systems such as CT or other x-ray based systems, SPECT systems, PET systems, and other imaging systems. Thus while the following discussion focuses on CT imaging systems, the method has wider application in other imaging arts.

Maximum likelihood reconstruction is a promising method to reduce the radiation dose applied to the patient in CT examinations. Such radiation dose reduction is achieved by accounting for the noise characteristics in the measured data to improve the signal-to-noise ratio. However, there is no analytic solution to the mathematical reconstruction problem, so iterative reconstruction techniques are often used for maximum likelihood reconstruction. Iterative reconstruction algorithms have a common structure. They model the forward projection of the original acquisition by assuming an image. This forward projection and the measured projection are evaluated for the calculation of difference or ratio functions, which could be, for example, the difference of the line integrals, or the difference of the number of photons at the detector, or some other measure. These differences or ratio functions lead to an update which improves the image in the sense that, for example, the difference between forward projection and measurement is minimized.

There are two kinds of iterative reconstruction methods. The first kind, such as for example the algebraic reconstruction technique (ART), simply solves a system of linear equations and does not account for the statistics of the measurements. The second kind of iterative reconstruction incorporates statistical reconstruction algorithms, such as the maximum likelihood methods, which offer the possibility to include the photon statistics in the reconstruction and try to match the theoretical model to the noisy data as closely as possible. The second approach results in a higher signal-to-noise ratio of the reconstructed images compared with analytical reconstruction algorithms at the same resolution.

Many iterative reconstruction techniques for CT require that the reconstruction algorithm iterates on the entire volume contributing to x-ray absorption, so the entire scan field-of-view (FOV) of the imaging system is reconstructed. For a typical CT system with non-truncated projections, the FOV is often a circular area of approximately 500 mm to 600 mm in diameter. Thus reconstructing the entire FOV demands a large number of voxels, especially in the case of a high resolution reconstruction, increasing the required computing power and time.

In some situations, however, the region-of-interest to the examiner or ROI is smaller than the entire FOV of the imaging system. One such situation is cardiac cone-beam CT, where the patient's heart defines the ROI. It is therefore known to iteratively reconstruct only the ROI plus a small transition range surrounding the ROI, for example as described by Andy Ziegler, Tim Nielsen and Michael Grass in "Iterative Reconstruction of a Region of Interest for Transmission Tomography", Med. Phys. 35(4), April 2008, pages 1317-1327, hereby incorporated by reference. Compared with a full FOV iterative reconstruction, such methods reduce the reconstruction time by reducing the number of voxels which are used for the reconstruction.

According to one aspect of the invention, a method and system are provided to generate an image of a region-of-interest. According to this aspect, imaging data are acquired to generate measured sinogram data, which is reconstructed to generate a bore reconstructed image. A region-to-iterate is identified in the bore reconstructed image, which includes a portion within a scan field-of-view of the imaging system and a portion outside the scan field-of-view. The region-to-iterate is removed from the bore reconstructed image to generate an intermediate image, which is forward projected to generate simulated partial sinogram data. The simulated partial sinogram data is subtracted from the measured full sinogram data to generate region-to-iterate sinogram data, which is reconstructed to generate an image of the region-of-interest.

The present invention reduces imaging artifacts which may arise using previously known region-of-interest reconstructions. Still further aspects of the present invention will be appreciated by those of ordinary skill in the art upon reading and understanding the following detailed description. Numerous additional advantages and benefits will further become apparent. The invention may take form in various components and arrangements of components, and in various process operations and arrangements of process operations. The drawings are only for the purpose of illustrating preferred embodiments and are not to be construed as limiting the invention.

Figure 1:
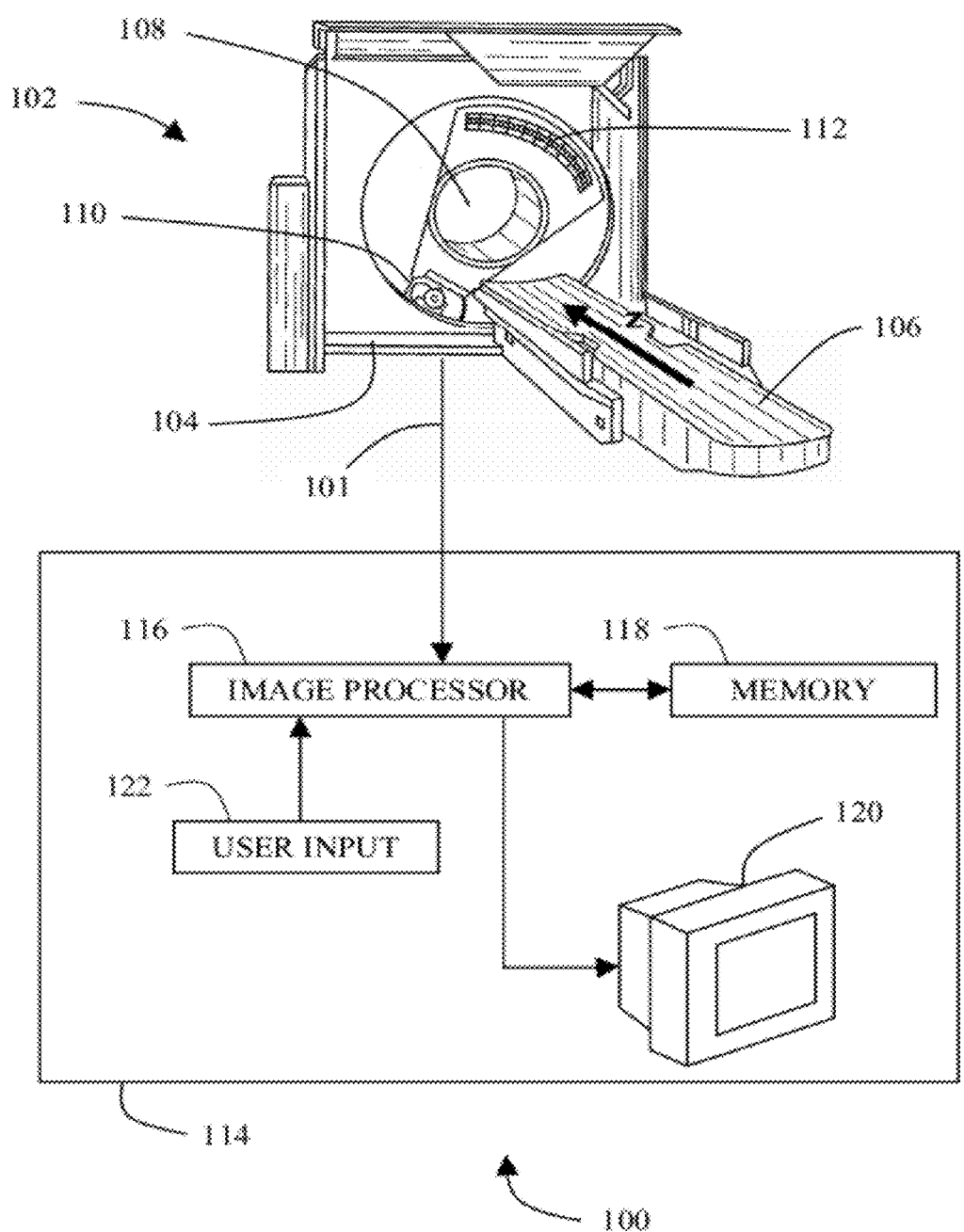
FIG. 1 illustrates an exemplary CT imaging system.

An exemplary CT imaging system 100 is shown in FIG. 1. A CT imaging acquisition system 102 includes a gantry 104 and a table or other support 106 which moves along the z-axis. A patient or other subject to be imaged (not shown in FIG. 1) lies down on the table 106 and is moved to be disposed within an aperture or bore 108 in the gantry 104. Once the patient is in position, an x-ray source 110 and an x-ray detector 112 rotate together around the bore 108 to record CT imaging data.

The CT imaging acquisition system 102 then passes the CT imaging data on to a CT imaging processing and display system 114 through a communication link 101. Although the systems 102 and 114 are shown and described here as being separate systems for purposes of illustration, they may in other embodiments be part of a single system. The CT imaging data passes to an image processor 116 which stores the data in a memory 118. The image processor 116 electronically processes the data to perform an image reconstruction, as described more fully below. The image processor 116 can show the resulting images on an associated display 120. A user input 122 such as a keyboard and/or mouse device may be provided for a user to control the processor 116.

Thus the aforementioned functions can be performed as software logic. "Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory such as memory 118, part of an operating system or other type of executable instructions. It will be appreciated by one of ordinary skill in the art that the form of software is dependent on, for example, requirements of a desired application, the environment it runs on, and/or the desires of a designer/programmer or the like.

The systems and methods described herein can be implemented on a variety of platforms including, for example, networked control systems and stand-alone control systems. Additionally, the logic shown and described herein preferably resides in or on a computer readable medium such as the memory 118. Examples of different computer readable media include Flash Memory, Read-Only Memory (ROM), Random-Access Memory (RAM), programmable read-only memory (PROM), electrically programmable read-only memory (EPROM), electrically erasable programmable read-only memory (EEPROM), magnetic disk or tape, optically readable mediums including CD-ROM and DVD-ROM, and others. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

Figure 2:
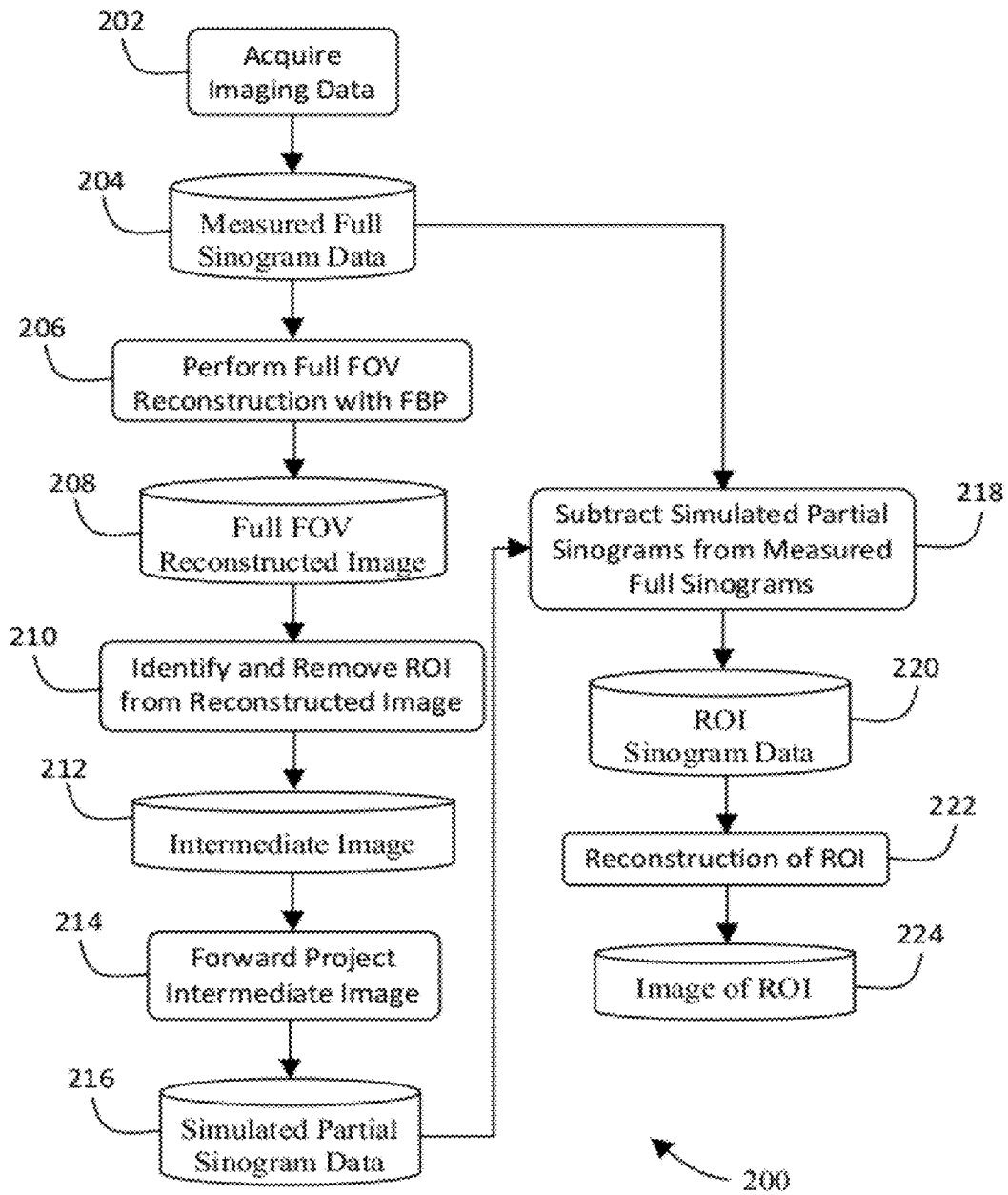
FIG. 2 illustrates the prior art method of Ziegler, et al. identified above.
Figure 3:
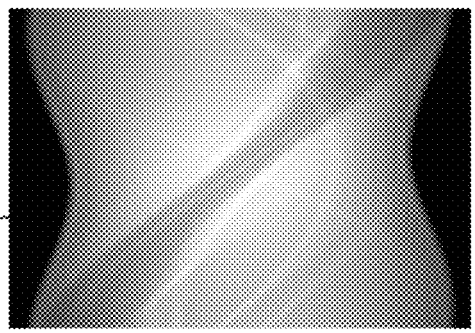
FIG. 3 is a representative example of a measured sinogram generated using a software simulation and the method of FIG. 2.

The prior art Ziegler et al. iterative ROI reconstruction method identified above is illustrated in FIG. 2. At step 202, imaging data is acquired for example by performing an imaging scan to generate measured full sinogram data 204. The data 204 represents a series of two-dimensional pictures taken by the x-ray detector 112 at various angular positions as it rotates around the imaged patient in the aperture 108. A representative example of a full measured sinogram 302 is shown in FIG. 3, which was generated with a software simulation of an actual image reconstruction using a mathematical head phantom as the imaged object.

Figure 4:
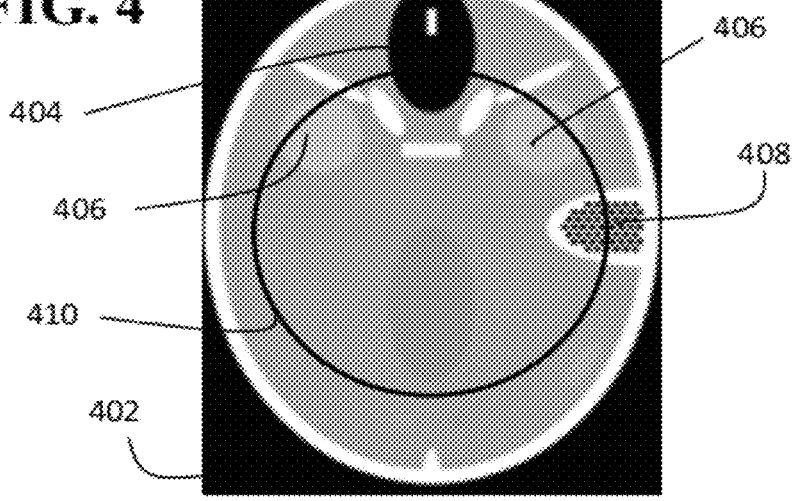
FIG. 4 is part of a full FOV reconstructed image generated using a software simulation and the method of FIG. 2.

Using the measured full sinogram data 204, a full reconstruction of the FOV is performed 206 using a non-iterative reconstruction algorithm such as filtered back projection. This results in a full FOV reconstructed image 208. A representative example of such a full FOV reconstructed image is shown in FIG. 4, which shows an image 402 of the mathematical head phantom used to generate the sinogram 302 of FIG. 3. Thus, the image 402 includes a simulated frontal sinus area 404, two simulated eyes 406, and one simulated inner ear 408.

Figure 5:
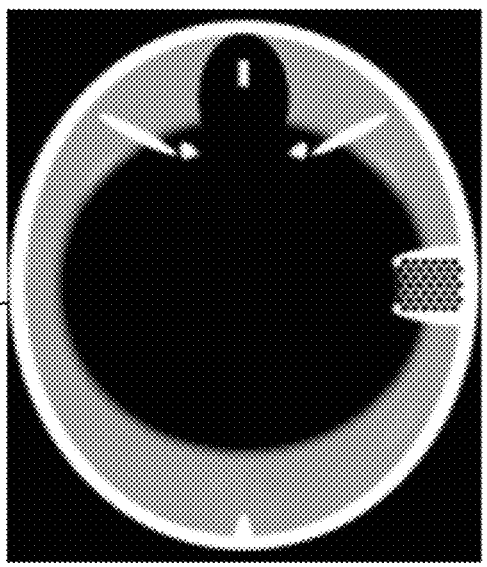
FIG. 5 is an intermediate image generated using a software simulation and the method of FIG. 2, wherein the ROI of FIG. 4 has been identified and removed.

The ROI within the full FOV reconstructed image 208 is then identified and removed 210. The ROI may be identified by a user interacting with a representation of the full FOV reconstructed image 208 displayed on a monitor 120. The ROI may alternatively be identified using conventional automated techniques to reduce or eliminate user involvement, or by any other technique. An ROI 410 is identified in FIG. 4. Once the ROI such as at 410 is identified, it is cut out 210 from the full FOV reconstructed image 208 preferably retaining a smooth transition to generate an intermediate image 212. A representative intermediate image 502 is shown in FIG. 5, where the ROI 410 has been removed from the full FOV reconstructed image 402 of FIG. 4.

Figure 6:
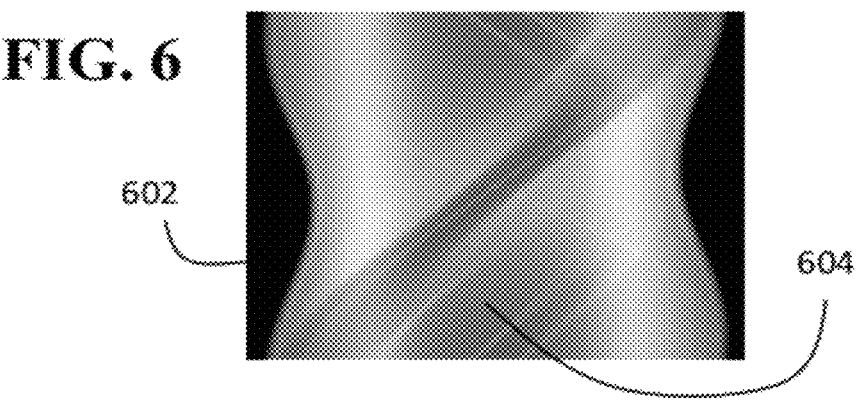
FIG. 6 is a simulated partial sinogram generated using a software simulation and the method of FIG. 2, from a forward projection of FIG. 5.

The intermediate image 212 is then forward projected 214 to generate simulated partial sinogram data 216. The data 216 represent a series of two-dimensional pictures which would have been taken by the x-ray detector 112 at various angular positions as it rotates around an object as shown by the intermediate image 212, that is, without the ROI being present. A representative example of a simulated partial sinogram 602 is shown in FIG. 6, which was generated by forward projecting the intermediate image 502 of FIG. 5. As can be seen, the simulated partial sinogram 602 differs from the full measured sinogram 302 in that it has a darker column 604 extending through its central region, as a result of cutting out the ROI in step 210. The forward projection step 214 generates several simulated two-dimensional pictures 216, each of which matches the angular position of one of the two-dimensional pictures of the full sinogram data 204.

Figure 7:
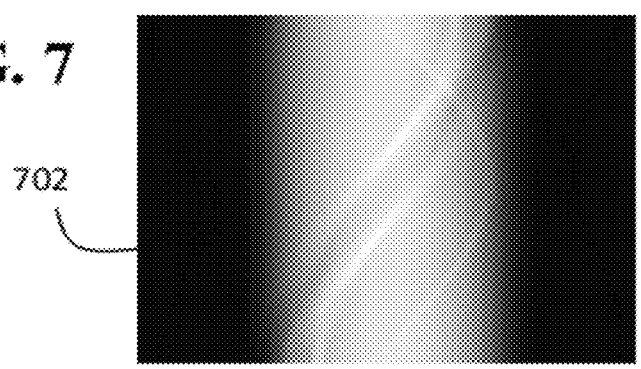
FIG. 7 is a representative example of an ROI sinogram generated using a software simulation and the method of FIG. 2, by subtracting FIG. 6 from FIG. 3.
Figure 8:
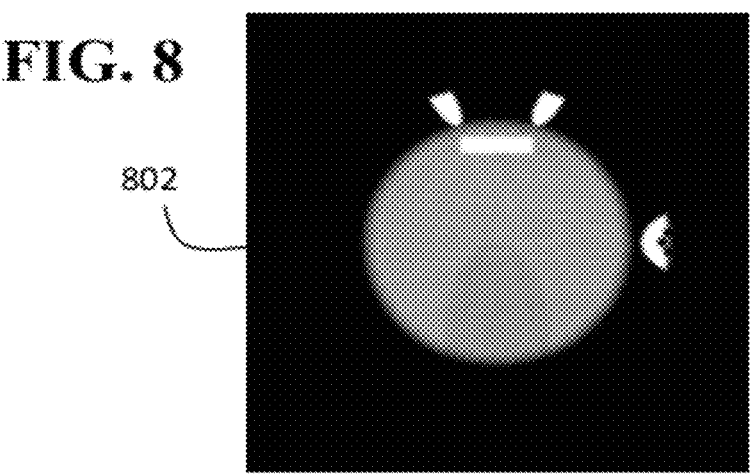
FIG. 8 is a representative example of a reconstructed image of an ROI generated using a software simulation and the method of FIG. 2.

The simulated partial sinogram data 216 are then subtracted 218 from the corresponding measured full sinogram data 204 at the same angle to generate ROI sinogram data 220. The data 220 represent a series of two-dimensional pictures which would have been taken by the x-ray detector 112 at various angular positions as it rotates around the ROI, including the smooth transition region around the ROI, but without the other parts of the object which are not of interest. A representative example of an ROI sinogram 702 is shown in FIG. 7, which was generated by subtracting the simulated partial sinogram 602 of FIG. 6 from the full measured sinogram 302 of FIG. 3. The ROI sinogram data 220 may then be analyzed by the image processor 116 using standard reconstruction techniques 222, such as an iterative reconstruction, to generate an image 224 of the ROI. In some cases, the reconstruction 222 may incorporate portions of the measured full sinogram data 204 in addition to the ROI sinogram data 220. See, for example, Patrick J. La Riviere, "Monotonic Iterative Reconstruction Algorithms for Targeted Reconstruction in Emission and Transmission Computed Tomography", 206 IEEE Nuclear Science Symposium Conference Record, pages 2924-2928, hereby incorporated by reference. A representative example of a reconstructed ROI image 802 is shown in FIG. 8, which was generated by reconstructing 222 the sinogram data 702 of FIG. 7.

One limitation of the prior art method in FIG. 2 is that it relies on a correct reconstruction of the image outside the ROI, generated in step 206. This is possible if non-truncated projections are provided in the measured full sinogram data 204, such as are available within the scan FOV of the imaging system 100. However, in many cases, objects are also present outside the scan FOV but within the bore 108 of the gantry 104. Such objects may include, for example, cables, parts of a blanket, parts of the patient, or even the patient table. In this situation, the prior art method of FIG. 2 cannot provide the desired sinogram of the ROI because only truncated projections are available to image objects outside the scan FOV. Thus the prior art iterative reconstruction of FIG. 2 is limited in that respect.

Figure 9:
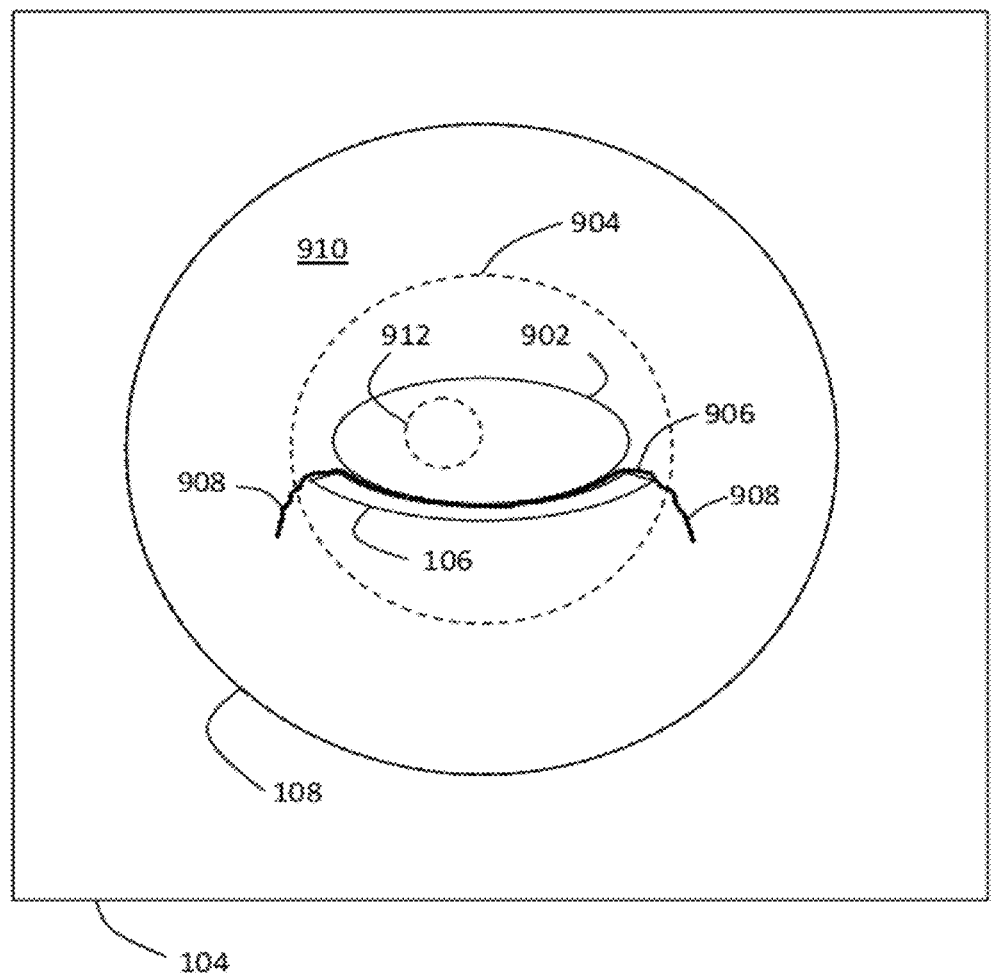
FIG. 9 illustrates the gantry of FIG. 1 having a patient on the table within the bore, and an object extending outside the scan FOV.

Such a situation is illustrated in FIG. 9, showing the gantry 104 of the CT imaging system 100 in FIG. 1, with a patient 902 disposed on the table 106 within the bore 108 of the gantry 104. A dotted circle represents the scan FOV 904 of the system 100, that is, the imaging area in which non-truncated projections can be measured by the x-ray detector 112 as it rotates around the bore 108. A blanket 906 is used for the comfort of the patient 902. Portions 908 of the blanket 906 extend outside the scan FOV 904 and into the ring 910 outside the scan FOV 904 but still within the bore 108. The x-ray detector 112 can gather imaging data for objects within the ring 910, like the portions 908 of the blanket 906, but such imaging data will be truncated. A representative ROI 912 within the patient 902, such as the cardiac region, is identified in FIG. 9 as well.

Figure 10:
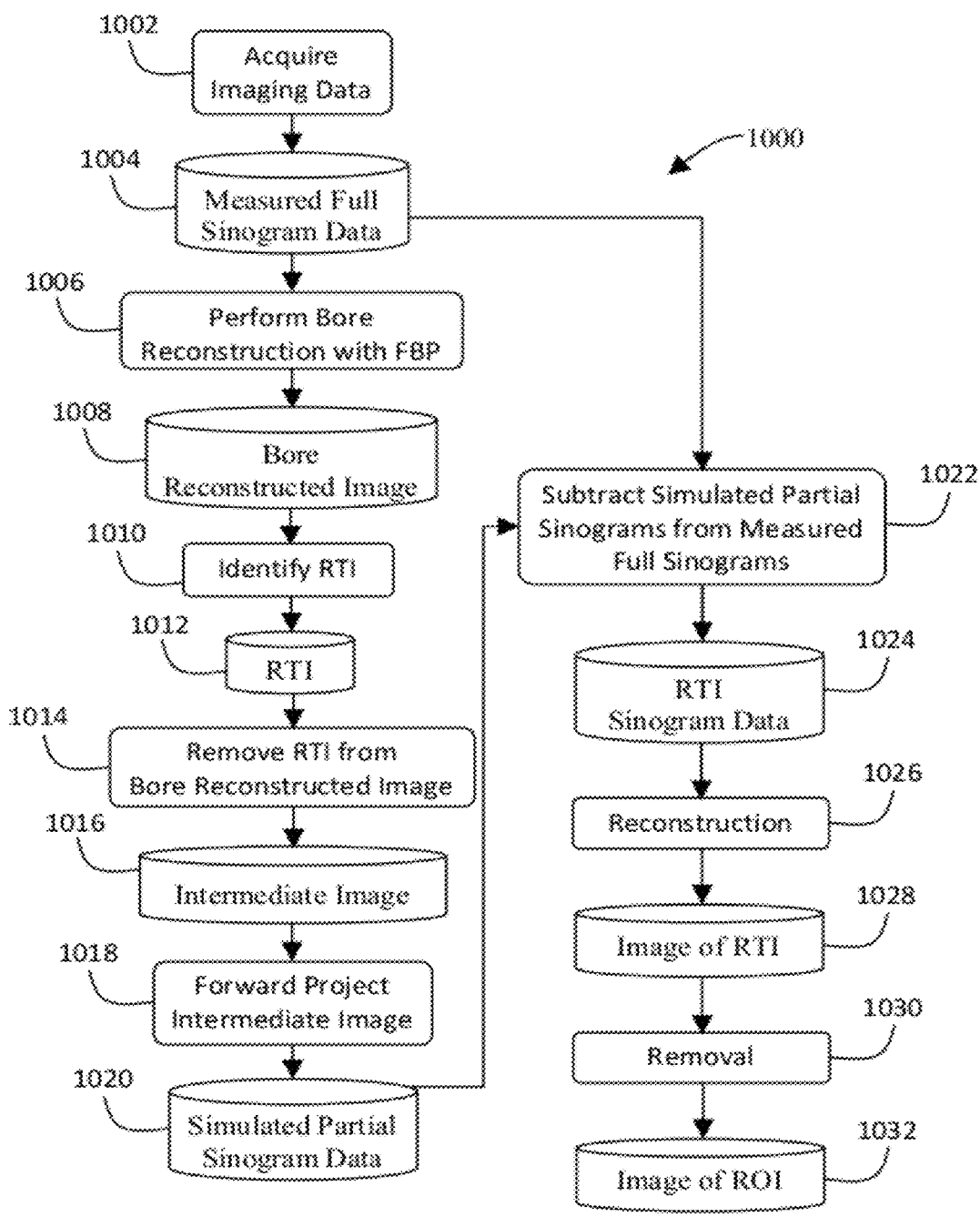
FIG. 10 illustrates a region-of-interest image reconstruction process according to one aspect of the present invention.

An exemplary region-of-interest image reconstruction process 1000 according to one aspect of the present invention is shown in FIG. 10, which may be used to generate an image of the ROI 912 even though portions 908 of the blanket 906 (and perhaps other objects) are present in the ring 910 outside the scan FOV 904.

At step 1002, imaging data is acquired for example by performing an imaging scan to generate measured full sinogram data 1004. The data 1004 represent a series of two-dimensional pictures taken by the x-ray detector 112 at various angular positions as it rotates around the imaged patient 902 in the bore 108.

At step 1006, and using the measured full sinogram data 1004, a full reconstruction of the imaging system bore 108 is performed. The reconstruction may be a conventional filtered back projection or other non-iterative reconstruction. This results in a bore reconstructed image 1008. Thus, as illustrated in FIG. 9 for example, the bore reconstructed image 1008 includes objects within the scan FOV 904 of the imaging system 100, such as the patient 902 and the table 106. The bore reconstructed image 1008 also includes other objects in the ring 910 outside of the scan FOV 904 but still within the bore 108 of the imaging system 100, such as the portions 908 of the blanket 906. The measured full sinogram data 1004 is non-truncated for objects within the scan FOV 904, but the data 1004 are truncated for objects within the ring 910 outside the scan FOV 904. Therefore, there will very likely be artifacts in the portions of the image 1008 which are within the ring 910.

The ROI within the bore reconstructed image 1008 is identified at step 1010. The region-of-interest may be for example the entire chest area of the patient 902 or other subject to be imaged, or perhaps just a portion thereof such as the cardiac region 912. In addition, imaged objects (or portions thereof) in the ring 910 outside the scan FOV 904 but within the bore 108 are also identified. Such objects may include, for example, the support table, cables, tubes, blankets, parts of the patient, and the like. The region-to-iterate or RTI 1012 is defined by the combination of the ROI with the objects (or portions thereof) in the ring 910. The RTI 1012 may be identified by a user interacting with a representation of the bore reconstructed image 1008 displayed on a monitor 120. The RTI 1012 may alternatively be identified using conventional automated techniques to reduce or eliminate user involvement, or by any other technique.

Figure 11:
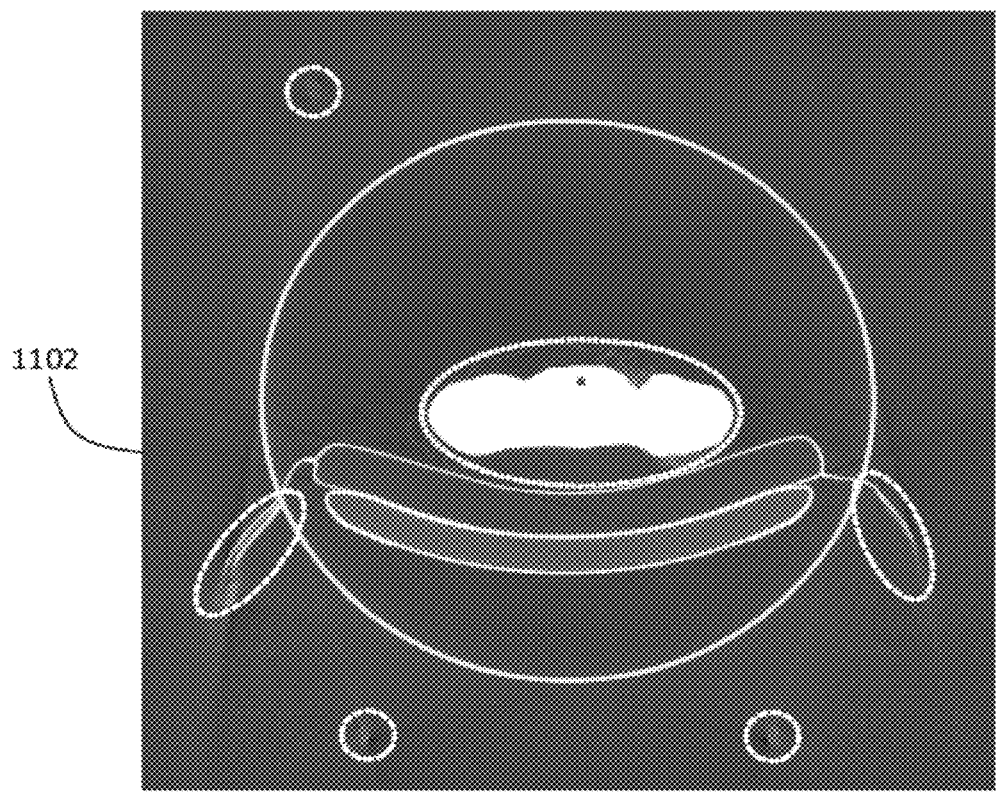
FIG. 11 is an image of a bore size reconstruction, illustrating a region-to-iterate (RTI).

For example, FIG. 11 is an image 1102 of a pediatric patient lying on top of a pillow blanket within a bore of an imaging system. The large, solid line circle corresponds to the scan FOV of the imaging system used to generate the image 1102. The dotted oval in the center of the image corresponds to the ROI, which in this case was the entire chest region of the patient. The remaining regions highlighted by dashes are two portions of the pillow blanket which extend outside the scan FOV, and well as three other objects which are outside the scan FOV but still within the bore of the imaging system. In the example of FIG. 11, the RTI 1012 corresponds to the dotted region in the center of the image, and the five dashed regions which are outside the scan FOV.

Once the RTI 1012 is identified, it is cut out 1014 from the bore reconstructed image 1008 preferably retaining smooth transition regions around the ROI and the objects within the ring 910, to generate an intermediate image 1016. As a matter of implementation, this may be accomplished by setting all voxel values in the RTI 1012 to zero, with a smooth weighting applied in the transition regions. The intermediate image 1016 is then forward projected 1018 to generate simulated partial sinogram data 1020, preferably in the acquisition geometry of the initial imaging scan 1002. However, other geometries may be used as well. The data 1020 represent a series of two-dimensional pictures which would have been taken by the x-ray detector 112 at various angular positions as it rotates around an object as shown by the intermediate image 1016, that is, without the RTI 1012 being present. The forward projection step 1018 generates several simulated two-dimensional pictures 1020, each of which matches the angular position of one of the two-dimensional pictures of the full sinogram data 1004.

The simulated partial sinogram data 1020 are then subtracted 1022 from the corresponding measured full sinogram data 1004 at the same angle to generate RTI sinogram data 1024. The data 1024 represent a series of two-dimensional pictures which would have been taken by the x-ray detector 112 at various angular positions as it rotates around the RTI 1012, including the smooth transition regions. The RTI sinogram data 1024 may then be analyzed by the image processor 116 using standard reconstruction techniques 1026, such as an iterative reconstruction, to generate an image 1028 of the RTI. In step 1030, portions in the RTI image 1028 which are not in the ROI are removed such as by subtraction, segmentation, region selection by a user, or the like. The remaining image data comprise an image of the ROI 1032. The reconstruction may be, for example, a maximum likelihood reconstruction, and may include using the measured full sinogram data 1004 in addition to the RTI sinogram data 1024.

Various embodiments of the present invention may include the previously discussed method steps in process 1000 in a variety of orders. In addition, various embodiments may include either more or less steps than the previously discussed method steps in process 1000.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof. The invention may take form in various components and arrangements of components, and in various steps and arrangements of steps. The drawings are only for purposes of illustrating the preferred embodiments and are not to be construed as limiting the invention.

Having thus described the preferred embodiments, then invention is now claimed to be:

1. An image reconstruction method to generate an image of a region-of-interest, the method comprising:
    acquiring image data relating to an imaged object in a bore of an imaging system to generate measured full sinogram data;
    using the measured full sinogram data to perform an image reconstruction of the bore and generate a bore reconstructed image, wherein the bore reconstructed image includes at least a portion of a first element within a scan field-of-view of the imaging system and at least a portion of a second element outside of the scan field-of-view but within the bore;
    identifying a region-to-iterate in the bore reconstructed image, wherein the region-to-iterate comprises a region-of-interest within the scan field-of-view as well as at least a portion of the second element outside of the scan field-of-view;
    removing the region-to-iterate from the bore reconstructed image to generate an intermediate image;
    forward projecting the intermediate image to generate simulated partial sinogram data;
    subtracting the simulated partial sinogram data from the measured full sinogram data to generate region-to-iterate sinogram data; and
    reconstructing the region-to-iterate sinogram data to generate an image of the region-of-interest.

2. The method of claim 1, wherein the image reconstruction of the imaging system bore is a non-iterative reconstruction.

3. The method of claim 2, wherein the image reconstruction of the imaging system bore is a filtered back projection reconstruction.

4. The method of claim 1, wherein at least a portion of the region-to-iterate is identified by a user.

5. The method of claim 1, wherein at least a portion of the region-to-iterate is identified with an automated technique.

6. The method of claim 1, wherein the removing step comprises retaining a smooth transition region around the region-of-interest in the bore reconstructed image.

7. The method of claim 1, wherein the forward projection of the intermediate image is performed in an acquisition geometry of an imaging scan.

8. The method of claim 1, wherein the reconstructing of the region-to-iterate sinogram data is an iterative reconstruction.

9. The method of claim 8, wherein the iterative reconstruction is a maximum likelihood reconstruction.

10. A system to perform a reconstruction to generate an image of a region-of-interest, the system comprising:
    an image processor; and
    a memory, the memory storing executable instructions, when executed by the image processor, causing the image processor to:
    receive measured full sinogram data generated from an imaging scan of an imaged object in a bore of an imaging system;
    use the measured full sinogram data to perform an image reconstruction of the bore and generate a bore reconstructed image, wherein the bore reconstructed image includes a region-of-interest within a scan field-of-view of the imaging system and at least a portion of a second element outside of the scan field-of-view but within the bore;
    wherein a region-to-iterate comprises the region-of-interest as well as at least a portion of the second element outside of the scan field-of-view;
    remove the region-to-iterate from the bore reconstructed image to generate an intermediate image;
    forward project the intermediate image to generate simulated partial sinogram data;
    subtract the simulated partial sinogram data from the measured full sinogram data to generate region-to-iterate sinogram data; and
    reconstruct the region-to-iterate sinogram data to generate an image of the region-of-interest.

11. The system of claim 10, wherein the image reconstruction of the imaging system bore is a non-iterative reconstruction.

12. The system of claim 11, wherein the image reconstruction of the imaging system bore is a filtered back projection reconstruction.

13. The system of claim 10, wherein at least a portion of the region-to-iterate is identified by a user.

14. The system of claim 10, wherein at least a portion of the region-to-iterate is identified with an automated technique.

15. The system of claim 10, wherein the removing step comprises retaining a smooth transition region around the region-of-interest in the bore reconstructed image.

16. The system of claim 10, wherein the forward projection of the intermediate image is performed in an acquisition geometry of the imaging scan.

17. The system of claim 10, wherein the reconstructing of the region-to-iterate sinogram data is an iterative reconstruction.

18. The system of claim 17, wherein the iterative reconstruction is a maximum likelihood reconstruction.

19. An image reconstruction method to generate an image of a region-of-interest, the method comprising:
    using a measured full sinogram data to perform an image reconstruction and generate an initial image, wherein the initial image includes a region-to-iterate, the region-to-iterate comprising a region-of-interest within a scan field-of-view and at least a portion of an element outside the scan field-of-view;
    removing the region-to-iterate from the initial image to generate an intermediate image;
    forward projecting the intermediate image to generate simulated partial sinogram data;

subtracting the simulated partial sinogram data from the measured full sinogram data to generate region-to-iterate sinogram data; and reconstructing the region-to-iterate sinogram data to generate an image of the region-of-interest.

* * * * *